United States Patent [19]

Freedman et al.

[11] Patent Number: 4,692,405
[45] Date of Patent: Sep. 8, 1987

[54] MONOCLONAL ANTIBODIES TO ANTIGEN ON ACTIVATED HUMAN B-CELLS AND ASSAY THEREFOR, PROTEIN ANTIGENIC DETERMINANT THEREFOR AND METHOD OF MAKING SAME

[75] Inventors: Arnold Freedman; Lee Nadler, both of Newton; Stuart Schlossman, Newton Center, all of Mass.

[73] Assignee: Dana-Farber Cancer Institute, Inc., Boston, Mass.

[21] Appl. No.: 708,176

[22] Filed: Mar. 5, 1985

[51] Int. Cl.[4] .................... G01N 53/00; G01N 33/53; C12P 21/00; C12N 5/00
[52] U.S. Cl. ......................... 435/7; 435/68; 435/240.27; 435/948; 435/172.2; 436/548; 436/808; 935/95; 935/106; 935/107; 935/108; 935/110; 530/387; 530/388
[58] Field of Search .............. 260/112 R, 112 B; 435/68, 240, 241, 948, 172.2, 7; 436/548, 808; 935/95, 106, 107, 108, 110; 530/387, 388

[56] References Cited

U.S. PATENT DOCUMENTS 4,444,744  4/1984  Goldberg .................... 424/1.1

OTHER PUBLICATIONS

Mittler et al, Journal of Immunology, vol. 131, No. 4, 1754–1761, 1983.
Chemical Abstracts, vol. 95, No. 3099m, 1981.
Chemical Abstracts, vol. 102, No. 60448m, 1985.
Chemical Abstracts, vol. 102, No. 22586x, 1985.
Thorley-Lawson et al., Cell, vol. 30, 415–425 (1982).
Yokochi et al., J. Immunol., vol. 128, 823–827 (1982).
Posnett et al., J. Immunol., vol. 133, 1635–1640 (1984).
Frisman et al., Blood, vol. 62, 124–1229 (1983).
Lazarovits et al., J. Immunol., vol. 133, 1857–1862 (1984).
Haynes et al., J. Immunol., vol. 126, 1409–1414 (1981).
Haynes et al., J. Immunol., vol. 127, 347–351 (1981).
Tedder et al., Journal of Immunology, vol. 133, No. 2, pp. 678–683 (1984).
Nadler et al., Journal of Immunology, vol. 126, No. 5, pp. 1941–1947 (1981).
Jung et al., J. Exp. Med., vol. 160, No. 6, pp. 1919–1924 (1984).

Primary Examiner—Robert J. Warden
Assistant Examiner—Patricia L. DeSantis

[57] ABSTRACT

A monoclonal antibody recognizing an antigenic determinant on activated human B-cells, the antigenic determinant being characteized in that it is a protein distinct from B-LAST-1 and BB-1, the antibody being substantially unreactive with unactivated human B-cells.

22 Claims, 7 Drawing Figures

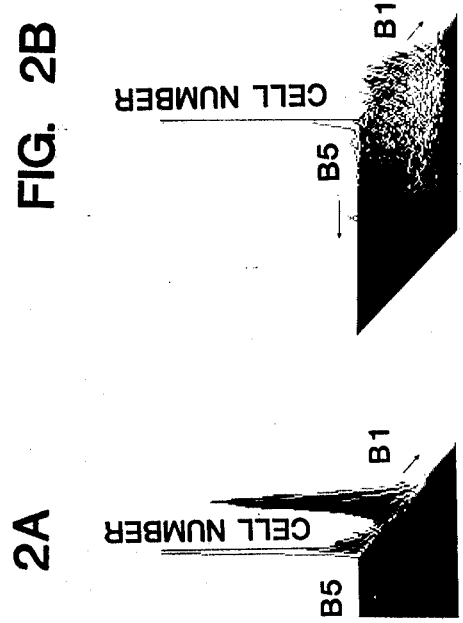

MONOCLONAL ANTIBODIES TO ANTIGEN ON ACTIVATED HUMAN B-CELLS AND ASSAY THEREFOR, PROTEIN ANTIGENIC DETERMINANT THEREFOR AND METHOD OF MAKING SAME

This invention was made with Government support and the Government has certain rights in the invention.

BACKGROUND OF THE INVENTION

This invention relates to monoclonal antibodies, to diagnostic methods employing monoclonal antibodies, and to the detection of activated B-cells.

B-lymphocytes are involved in the humoral, or circulating, immune response to the extracellular phases of bacterial and viral infection. When activated by exposure to specific antigenic or mitogenic stimuli, human B-lymphocytes proliferate and subsequently differentiate into antibody secreting cells. During the stages of activation, B-cells increase in size, synthesize both DNA and RNA, and undergo changes in cell surface structures. Neoplastic changes in B-cells, e.g., leukemias or lymphomas of B-cell origin, also induce changes in the expression of cell surface antigens.

Thorley-Lawson et al., (1982) Cell 30:415-425 describe a B-cell restricted antigen (B-LAST-1) which appears on the surface of B-lymphocytes 2-3 days after stimulation with mitogens or Epstein-Barr Virus (EBV). B-LAST-1 is a single chain polypeptide with a molecular weight of 45 kd. B-LAST-1 is also found on chronic lymphocytic leukemia (CLL) cells and poorly differentiated lymphoma cells. The isotype of anti-B-LAST-1 monoclonal antibody of murine origin was reported to be IgG2b.

Yokochi et al., (1982) J. Immunol. 128:823-827 report a B-cell antigen, BB-1, which appears on the surface of EBV and mitogen-activated human and some non-human primate B-cells. The molecular weight of the BB-1 antigen is 37,000. Expression was detected 4-5 days post-EBV-activation and peaked at 7 days. BB-1 was also found on 50% of the myelomas tested.

SUMMARY OF THE INVENTION

The present invention provides a monoclonal antibody recognizing an antigenic determinant on activated human B-cells, the antigen being characterized in that it is a protein distinct from B-LAST-1 (described in Thorley-Lawson et al., (1982) Cell 30:415-425) and from BB-1 (described in Yokochi et al., (1982) J. Immunol 128:823-827). The antibody is substantially unreactive with unstimulated human B-cells.

The present invention also provides a substantially pure protein having an antigenic determinant or determinants substantially identical to determinants of a single-chain polypeptide having an apparent molecular weight of approximately 75,000 daltons under reducing conditions and 67,000 daltons under non-reducing conditions, the single-chain polypeptide being a protein on the surface of activated human B-cells.

In another aspect the invention provides a process for preparing the antigenic protein which comprises culturing peripheral or splenic human B-cells activated with Epstein-Barr virus, pokeweed mitogen, protein A, or anti-immunoglobulin, or culturing Burkitt's lymphoma cell line Ramos or the plasma cell leukemia line RPMI 8226, and isolating the protein from these cells.

The invention also provides kits useful for assaying a biological sample for the presence of cells expressing the antigen of the invention and for assaying a biological sample for the presence of antibody to the cells expressing the antigen of the invention. These kits contain one or more containers, each holding separately detectably labeled or unlabeled antibody or antigen of the invention, and in another compartment, a means for detecting the formation of immunocomplexes.

DESCRIPTION OF PREFERRED EMBODIMENTS

In the drawings,

FIG. 2 is a pair of histograms showing the reactivity of anti-B1 and anti-B5 monoclonal antibody to splenic B-cells before (A) and after activation with anti-Ig antibody (B);

PREPARATION OF ACTIVATED B-CELLS

Figure 1:
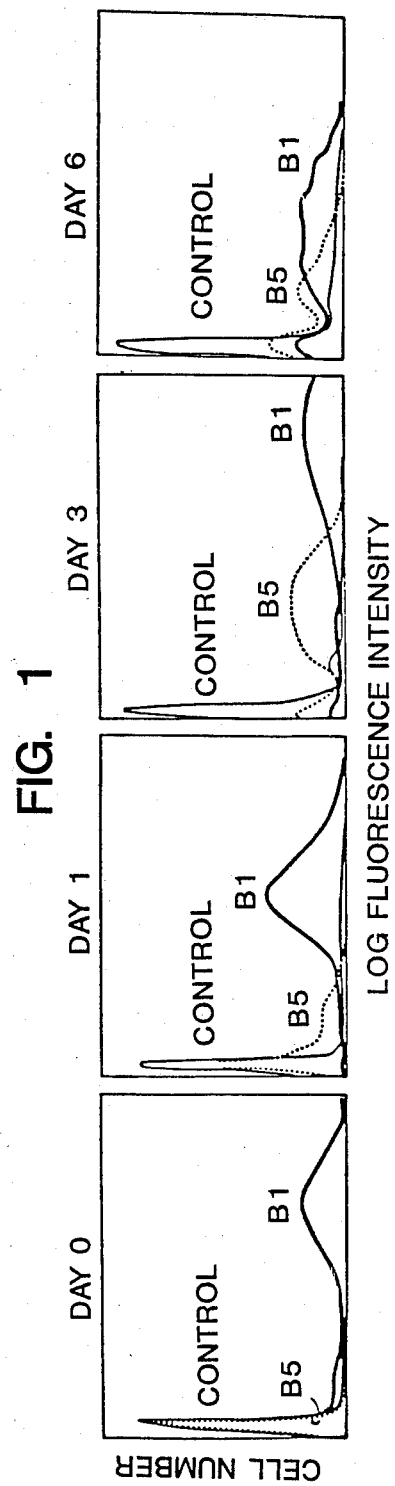
FIG. 1 is a series of histograms showing the reactivity of anti-B1 and anti-B5 monoclonal antibody to splenic B-cells activated with anti-Ig antibody.

Normal human splenic B-lymphocytes were cultured at $1.5 \times 10^6$ cells/ml in RPMI 1640 supplemented with 10% FCS, 2 mM glutamine, 1 mM sodium pyruvate in tissue culture flasks for 1, 3, and 6 days with four different stimuli. (1) Pokeweed mitogen (PWM): at a final concentration of 1:300. For days, 1, 3, and 6 whole splenic mononuclear cells were used. (2) Anti-Ig: Affinity purified rabbit anti-human Ig was coupled to Affigel 702 beads, specificity was checked by testing Affigel 702 beads which has been conjugated to bovine serum albumin, anti-B1, or anti-B2 antibody, none of which showed any B cell stimulation. For the day 1 and day 3 stimulations, anti-Ig beads were incubated with highly purified B cells which were obtained by lysing the E rosette negative fraction of splenic mononuclear cells with anti-Mo1, anti-Mo2, anti-T4, and anti-T8 followed by complement. The day 6 stimulation utilized unfractionated splenic mononuclear cells. (3) Protein A: Protein A was used at a final concentration of 10 g/ml. As described above, highly purified B cells were cultured for 1 and 3 days at a concentration of $1.5 \times 10^6$/ml. The day 6 stimulation utilized unfractionated splenic mononuclear cells. (4) EBV: The E rosette negative fraction of splenic mononuclear cells were cultured with EBV (1:4 diluted supernatant from the EBV-producing marmoset cell line B955) for 1, 3, and 6 days. Prior to phenotypic analysis of all activated samples, the cells were harvested and lysed with anti-Mo1, anti-Mo2, anti-T4, and anti-T8 followed by complement to clear monocytes and T-cells respectively and enrich the B-cell fraction from the samples.

PREPARATION OF ANTI-B5 MONOCLONAL ANTIBODY

A 6 week old female BALB/C mouse was immunized i.p. with $5 \times 10^6$ cryopreserved B cell diffuse histiocytic lymphoma (DHL) cells in phosphate-buffered saline (PBS). These tumor cells were of B cell origin in that they expressed monoclonal cell surface IgM, k, as well as the B cell associated antigens Ia, B1, and B4. In contrast, these tumor cells were unreactive with monoclonal antibodies directed against the common acute leukemia antigen (CALLA); T cell antigens T3, T4, T8, and T11; and the myeloid/monocyte antigens Mo1, Mo2, and MY7. Twenty eight days later, the animal was boosted with $5 \times 10^6$ tumor cells i.v. and somatic cell hybridization was carried out 4 days later by the method of Kohler and Milstein (Nature, (1977) 256:495) with modifications as described in Nadler et al., J. Immunol. (1980) 125:570. Mouse splenocytes ($1.5 \times 10^8$) were fused with 30% polyethylene glycol and Dulbecco's MEM with $2 \times 10^7$ P3/NS1/1-Ag4-1 myeloma cells. After fusion, cells were cultured in aminopterin-containing medium at 37° in a 5% $CO_2$ humid atmosphere. Ten to 28 days later, approximately 300 macroscopic clones were identified, 125 of which were reactive with the immunizing DHL cells, measured by indirect immunofluorescence. In brief, 0.5 to $1 \times 10^6$ viable washed DHL cells were treated with 100 ul of supernatant from hybridoma cultures exhibiting growth, incubated at 4° C. for 30 minutes and washed three times. The cells were then treated with 100 ul of 1:50 dilution of goat anti-mouse IgG and goat anti-mouse IgM conjugated with fluorescein isothiocyanate incubated at 4° for 30 minutes, washed three times, analyzed on an EPICS V cell sorter. The percent positive cells were determined using the EASY Immuno-program. Producer clones were then screened on a panel of fractionated peripheral blood and tumor cells. One hybrid clone, designated anti-B5 was found to react with the immunizing DHL cells, several other B cell DHL cell lines, but was unreactive with fractionated peripheral blood mononuclear cells. Hybrid clone anti-B5 was then subcloned three times by limiting dilution and passaged into BALB/C mice to produce a malignant ascites. Supernatant and ascites anti-B5 were shown to have a similar reactivity pattern by indirect immunofluorescence. The B5 ascites demonstrated reactivity with the immunizing DHL cells to a dilution of 1/20,000 that diminished to background at 1/50,000. The B5 antibody was determined to be of the murine IgM isotype. In all subsequent experiments, B5 ascites were used.

DEPOSIT

The anti-B5-producing hybridoma cell line, designated Hybridoma B5, has been deposited in the American Type Culture Collection, Rockville, MD, and given ATCC Accession No. HB 8716 dated Feb. 8, 1985.

EXPRESSION OF ACTIVATED B-CELL SURFACE ANTIGEN

As shown in Table I, prior to culturing, cells did not express B5. In the presence of media alone, approximately 10–15% of cells expressed B5 after three days of culture, although the viability of these cells was only 10–20%. When stimulated with Protein A, anti-Ig antibody or EBV as shown in FIG. 1 (viability approximately 70–80%) about 10–15% of cells weakly expressed B5 after 1 day, while 65% of cells expressed the antigen more intensely by 3 days of culture. The level of expression of B5 by day 6 was similar to day 1, and by day 10 (in the presence of anti-Ig antibody), B5 antigen expression was again background level. PWM did not appear to induce cells to express B5 as well as anti-Ig antibody, EBV, or protein A, with the number of cells being only two-fold over background.

TABLE

EXPRESSION OF B5 AND B1 ANTIGENS ON SPLENIC B CELLS STIMULATED IN VITRO*

| Day | Antigen tested | % positive cells when stimulated in vitro | | | | |
|---|---|---|---|---|---|---|
| | | Media | Protein A | Anti-IgG | EBV | PWM |
| 0 | B1 | 80 | 80 | 80 | 80 | 80 |
| | B5 | <5 | <5 | <5 | <5 | <5 |
| 1 | B1 | 74 | 68 | 80 | 84 | 56 |
| | B5 | 6 | 38 | 14 | 12 | 18 |
| 3 | B1 | 44 | 78 | 90 | 80 | 69 |
| | B5 | 10 | 43 | 68 | 64 | 25 |
| 6 | B1 | 46 | 48 | 57 | 71 | 31 |
| | B5 | 2 | 5 | 16 | 24 | 4 |

*one of three experiments showing identical patterns of induction of B5 expression.

In order to further demonstrate that B5 was expressed on activated B cells, splenic mononuclear cells enriched for B cells were stimulated for 3 days with anti-Ig conjugated to beads. Viable cells were harvested and labelled with directly fluoresceinated anti-B1 and directly biotinylated anti-B5 developed with Texas-Red-Avidin, and then evaluated by dual laser flow cytometric analysis. As shown in FIG. 2, panel A unstimulated cells only expressed the B1 antigen and failed to express B5. After three days in culture with anti-Ig, all cells expressing B5 co-expressed the B1 antigen.

B5 is expressed on cell lines and tumor cells of B-cell origin. As shown in Table 2, anti-B5 was reactive with cell lines of B lineage including all EBV transformed lymphoblastoid B cell lines, Burkitt's lymphoma lines, four of five DHL lines and the plasma cell leukemia cell line RPMI 8226. The non-T-cell ALL line Laz 221, and the CML blast crisis line Nalm 1, both known to be of early neoplastic B cell origin, were unreactive with anti-B5. No reactivity was found on T-cell lines or an Ia+ T-cell clone. These results as well as the lack of expression of B5 myeloid cell lines HL-60, KG-1, U937, and SU-DHL 1 and the erythroid cell line K562 indicate that anti-B5 has restricted reactivity to cells of B cell derivation.

TABLE 2

| Cell Lines | Line designation | Degree of positivity with monoclonal antibody | | | | | |
|---|---|---|---|---|---|---|---|
| | | B5 | B1 | B2 | B4 | k/l | Ia |
| EBV lymphoblastoid | 156 | + | +++ | + | ++ | +++ | +++ |
| | SB | ++ | +++ | + | ++ | +++ | +++ |
| Burkitt's | Raji | ++ | +++ | ++ | ++ | +++ | +++ |
| | Ramos | +++ | +++ | 0 | + | +++ | 0 |
| | Daudi | +++ | +++ | 0 | + | +++ | +++ |
| Non-T Cell ALL | Laz 221 | 0 | 0 | 0 | ++ | + (μ) | +++ |
| CML Blast Crisis | Nalm-1 | 0 | + | 0 | ++ | + (μ) | +++ |
| DHL | SU-DHL 1 | 0 | 0 | 0 | 0 | 0 | 0 |
| | SU-DHL 2 | + | +++ | 0 | 0 | 0 | 0 |
| | SU-DHL 4 | ++ | +++ | 0 | ++ | +++ | +++ |
| | SU-DHL 6 | ++ | +++ | 0 | ++ | +++ | +++ |
| | SU-DHL 8 | + | 0 | 0 | ++ | + | +++ |
| Myeloma | RPMI 8226 | +++ | 0 | | ++ | 0 | +++ |

TABLE 2-continued

| Cell Lines | Line designation | Degree of positivity with monoclonal antibody | | | | | |
|---|---|---|---|---|---|---|---|
| | | B5 | B1 | B2 | B4 | k/l | Ia |
| | MeCar | 0 | ++ | 0 | ++ | 0 | +++ |
| T-ALL | HSB | 0 | 0 | 0 | 0 | 0 | 0 |
| | CEM | 0 | 0 | 0 | 0 | 0 | 0 |
| Ia + T cell | EL 156 | 0 | 0 | 0 | 0 | 0 | +++ |
| Myeloid | HL-60 | 0 | 0 | 0 | 0 | 0 | 0 |
| | KG-1 | 0 | 0 | 0 | 0 | 0 | ++ |
| | U 937 | 0 | 0 | 0 | 0 | 0 | 0 |
| Erythroid | K 562 | 0 | 0 | 0 | 0 | 0 | 0 |

$^a$Degree of positivity was qualitatively assessed by flow cytometry. 0, no detectable reactivity over background; +, designated weak to moderate (B5 on day 1, FIG. 2); ++, designated strong (B5 on day 3, FIG. 2); +++, strongestreactivity (B1 on day 3, FIG. 2).

The reactivity of anti-B5 with a variety of B-cell malignancies was next investigated (Table 3). This series of neoplasms represent stages of normal B cell differentiation. All of the non-T-cell acute lymphoblastic leukemias (ALL) tested were of B-cell origin by expression of Ia and B4. None of these early neoplastic B-cells expressed B5. About half of the B cell chronic lymphocytic leukemias (CLL) and DHLs examined, expressed B5, with a smaller percentage of poorly differentiated lymphocytic lymphomas (PDL) expressing the antigen. With the lack of expression of B5 on the Waldenstrom's macroglobulinemia cells and myelomas examined, the expression of B5 antigen was limited to cells which correspond to the mid stages of normal B cell differentiation. Cells from patients with T cell derived ALL, CLL, and T cell non-Hodgkin's lymphoma, including lymphoblastic lymphoma and DHL were unreactive with anti-B5. The B5 antigen was also not expressed on cells from patients with acute myeloblastic leukemia (AML). These observations confirm the B cell specificity of B5 and indicate that B5 is expressed on populations of B lymphocytes in the mid stages of normal B cell differentiation.

TABLE 3

| Disease | # of patient samples | # of patients reactive with monoclonal antibody | | | | |
|---|---|---|---|---|---|---|
| | | B5 | B4 | B1 | Ia | T3 |
| B Cell | | | | | | |
| Non-T ALL | 21 | 0 | 21 | 8 | 21 | 0 |
| B-CLL | 24 | 12 | 24 | 24 | 24 | 0 |
| DHL | 18 | 8 | 18 | 18 | 18 | 0 |
| PDL-N | 7 | 5 | 7 | 7 | 7 | 0 |
| PDL-D | 8 | 0 | 8 | 8 | 8 | 0 |
| Waldenstrom's | 2 | 0 | 2 | 2 | 2 | 0 |
| Myeloma | 2 | 0 | 0 | 0 | 0 | 0 |
| T Cell | | | | | | |
| ALL | 8 | 0 | 0 | 0 | ND | 8 |
| CLL | 3 | 0 | 0 | 0 | 0 | 3 |
| NHL* | 5 | 0 | 0 | 0 | 2 | 5 |
| Myeloid | | | | | | |
| AML/AMMOL | 12 | 0 | 0 | 0 | 12 | 0 |

*Waldenstrom's macroglobulinemia
*Includes lymphoblastic lymphoma and T cell DHL

REACTIVITY OF ANTI-B5 MONOCLONAL ANTIBODY

The reactivity of anti-B5 to unactivated fractionated peripheral blood cells, and normal lymphoid and myeloid tissues was examined. Less than 1% of peripheral blood mononuclear cells (PBMC) isolated by Ficoll-Hypaque density sedimentation expressed the antigen, (Table 4) whereas they demonstrated significant reactivity with monoclonal antibodies directed against B-cell, T-cell, and monocyte antigens.

TABLE 4
REACTIVITY OF ANTI-B5 WITH RESTING LYMPHOID AND MYELOID CELLS

| Cell | # of tests | % of cells expressing antigen | | | | |
|---|---|---|---|---|---|---|
| | | B5 | B1 | T3 | Mol | Ia |
| Peripheral blood | | | | | | |
| PBMC | 4 | 1 ± 1 | 5 ± 2 | 50 ± 5 | 31 ± 8 | 18 ± 4 |
| E+ (T) | 6 | 1 ± 1 | 1 ± 1 | 90 ± 5 | 8 ± 3 | 2 ± 1 |
| E− nonadherant (B) | 3 | 1 ± 1 | 22 ± 4 | 2 ± 1 | 24 ± 3 | 42 ± 5 |
| Monocyte | 3 | 1 ± 1 | 2 ± 1 | 9 ± 3 | 54 ± 6 | 71 ± 5 |
| Granulocyte | 5 | 0 ± 1 | 1 ± 1 | 0 ± 1 | 88 ± 10 | 1 ± 1 |
| RBC | 3 | 0 ± 1 | 0 ± 1 | 0 ± 1 | 0 ± 0 | 0 ± 0 |
| Platelet | 3 | 0 ± 1 | 0 ± 1 | 0 ± 1 | 0 ± 1 | 0 ± 1 |

Figure 3C:
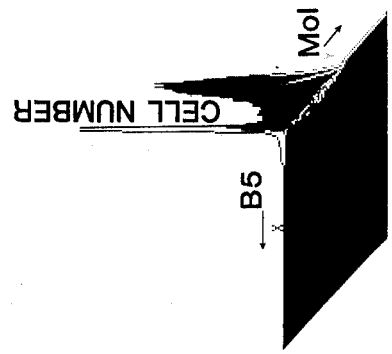
FIG. 3 is a series of histograms showing the reactivity of anti-B1 and anti-B5 monoclonal antibody to splenic B-cells unactivated (A) and activated with anti-Ig antibody (B), and unactivated monocytes (C)
Figure 3B:
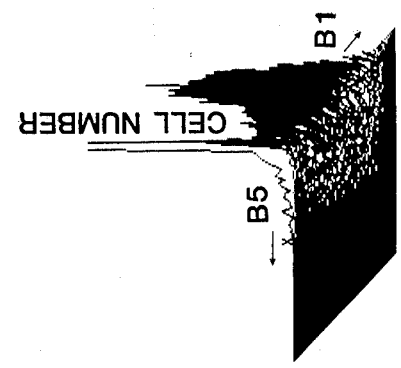
Figure 3A:
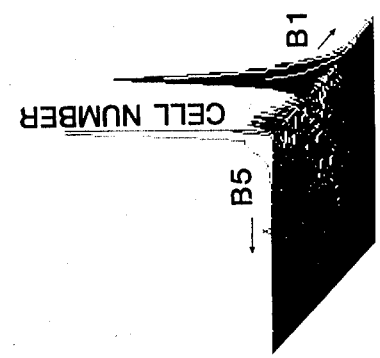

T-cells isolated by E rosetting similarly lacked detectable B5 expression. The E rosette negative fraction containing B-cells, monocytes, and null cells was further enriched for B-cells by adherence. The B-cell-enriched PBMC were stained with directly fluoresceinated anti-B1 and directly biotin-conjugated anti-B5 developed with Avidin Texas Red. Utilizing dual laser flow cytometic analysis, cells were examined as shown in FIG. 3, before (Panel A) and after 3 days of stimulation with anti-Ig antibody (Panel B). As seen in Panel A very few dual labelled cells were observed, whereas in Panel B clearly demonstrated B1+B5+ cells could be detected. In addition, monocytes were stained with directly fluoresceinated anti-Mo1 and directly biotin-conjugated anti-B5 developed with Avidin Texas Red (Panel C) and similarly analyzed. Adherent monocytes were noted to weakly express B5 on 10–20% of cells analyzed. However, when monocytes were incubated in 10% human serum for 1 hour prior to phenotyping, no cells appeared to co-express B5 and Mo1. Similarly granulocytes, RBC and platelet preparations lacked reactivity with anti-B5. The percentage of B5 bearing Ficoll-Hypaque mononuclear cells within lymphoid tissues is enumerated in Table 5.

TABLE 5

REACTIVITY OF ANTI-B5 WITH LYMPHOID TISSUES

| Tissue | # of tests | % of cells reactive with monoclonal antibody | |
|---|---|---|---|
| | | B5 | B1 |
| Lymph node | 4 | 6 ± 2 | 28 ± 8 |
| Spleen (whole) | 7 | 2 ± 1 | 45 ± 5 |
| Spleen (E−) | 3 | 5 ± 3 | 72 ± 12 |
| Tonsil | 3 | 4 ± 2 | 54 ± 9 |
| Thymus | 3 | 0 ± 1 | 0 ± 1 |
| Bone marrow | 3 | 1 ± 1 | 6 ± 3 |

Mononuclear cells isolated from normal lymph node, tonsil, and spleen were weakly reactive with anti-B5, with less than 6% of cells analyzed being positive. The E-population of normal spleen of which 70-80% of cells express the B1 antigen, similarly weakly expressed B5. Mononuclear cells from thymus and bone marrow were unreactive with anti-B5.

Reactivity of anti-B5 monoclonal antibody to activated fractionated peripheral blood cells was also determined. B-cells were prepared by E rosetting, adherence, and then lysis of the remaining cells with anti-T-cell (T4 and T8) and anti-monocyte (Mo1 and Mo2) antibodies and complement. This B cell enriched fraction (50% B1+) was cultured in the presence of anti-Ig antibody conjugated to beads. At 3 days, these cells (60% B1+) were harvested and the viability ranged between 60 and 80%. These cells were considered activated since they were proliferating as measured by uptake of $H^3TdR$ (stimulation index=5-10) and morphologically approximately ⅔ of cells now were enlarged with a lymphoblastoid appearance. The cells were then examined by indirect immunofluorescence and flow cytometric analysis for B5 expression. In contrast to resting peripheral blood B-cells, approximately 25% of cells now expressed B5. In order to demonstrate that B5 expression was limited to activated B-cells, cells were labelled with anti-B1 directly conjugated to fluorescein and anti-B5 conjugated to biotin then developed with Texas-Red-Avidin. Utilizing dual laser flow cytometric analysis, it was clearly shown that the majority of unstimulated cells only expressed B1 with rare cells expressing B1 and B5 (FIG. 3). However, after 3 days of culture with anti-Ig antibody, 25% of cells expressed B5 and all cells expressing B5 co-expressed B1. In contrast, T cells isolated by E rosetting, were cultured with PHA for six days. Viable cells were isolated and the cell surface phenotype examined after 2 and 6 days of stimulation. These cells were uniformly T cells by their strong expression of T11 and were activated as determined by their expression of Ia (30% of cells expressed Ia at day 6) and IL-2 receptor (90% of cells expressed IL-2R at day 2, 70% at day 6). These activated T-cells demonstrated no detectable B5 antigen. Similarly monocytes were activated overnight with PHA-leukocyte conditioned medium (PHA-LCM), and although these cells strongly expressed Mo1, Mo2, and Ia, they did not express B5.

BIOCHEMICAL CHARACTERIZATION OF B5

Burkitt's lymphoma cell line Ramos, and the plasma cell leukemia cell line RPMI 8226, were used for the isolation of the B5 cell surface antigen. A modification of the lactoperoxidase conjugation iodination technique as described by Boyd et al., J. Immunol (1981) 126:2461 was used to label cell surface proteins with $I^{125}$. The iodinated cells obtained from this procedure were washed twice with cold PBS and lysed on ice with cell lysis buffer (50 mM Tris HCl, 0.4M NaCl, 1% Triton X-100, 2 mM DMSF, 5 mM EDTA, 50 mM iodoacetamide, pH 8). After 30 minutes the lysate was centrifuged at 800 g for 10 minutes to remove unlysed cells, nuclei, and other insoluble material. The supernatant was frozen at −80° C. until analyzed by immunoprecipitation.

Figure 4:
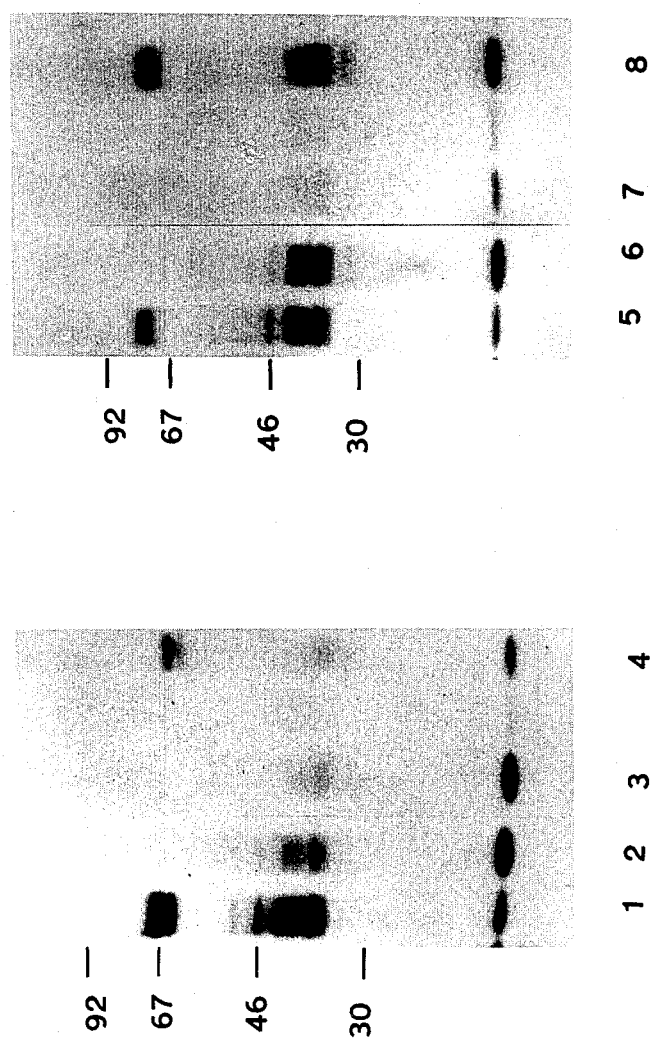
FIG. 4 is an SDS-PAGE characterization of labeled cell surface proteins immunoprecipitated with anti-B5 monoclonal antibody.

Cell supernatants and cell lysates were centrifuged at 10,000 g for 30 minutes and transferred to fresh test tubes. Prior to immunoprecipitation of cell lysates were mixed with 20 mg of rabbit anti-human Ig antibody and pre-cleared four times; twice, for 1 hour at 4° C., with PANSORBIN S. Aureus Cells once with SEPHAROSE 4B beads and finally with preformed complex of rabbit anti-mouse antibody and an irrelevant mouse immunoglobulin. The pre-cleared samples were mixed with either: (1) Anti-B5 rabbit anti-mouse Ig complexes. (2) An irrelevant monoclonal IgM complex with rabbit anti-mouse Ig. (3) B5-conjugated SEPHAROSE beads or (4) Irrelevant IgM-conjugated beads SEPHAROSE 4B beads. The mixtures were held on ice for 2 hours at 0° C. after which the samples were centrifuged at 10,000 g for 5 minutes and the supernatants discarded. The pellets were washed four times in 1% TRITON (octyl phenoxy polyethoxy ethanol) X-100/0.2% sodium deoxycholate in RIPA buffer (0.2 sodium phosphate, 5 mM EDTA, 5 mM EGTA, 1 mM NaF, pH 7.4). As shown in FIG. 4, the precipitates were analyzed by 10% SDS-polyacrylamide gel electrophoresis under non-reducing (lanes 1-5) and reducing (50 mM dithiothreitol) (lanes 6-10) conditions. Ramos cell lines: Anti-B5 conjugated to SEPHAROSE 4B beads 4B (lanes 1 and 5) was compared with an irrelevant antibody conjugated to Sepharose 4B (lanes 2 and 6). RPMI 8226 cell line: Anti-B5 rabbit anti-mouse Ig preformed complexes (lanes 4 and 8) were compared to irrelevant antibody rabbit anti-mouse Ig preformed complexes (lanes 3 and 7). The apparent molecular weights (m.w.) of B5 at 75 kilodaltons (Kd) under reducing and 67 Kd under non-reducing conditions, reflect the presence of interchain disulfide bonds. (This biochemical characterization of the B5 antigen shows that it is a single chain cell surface protein.)

USE

The monoclonal antibody of the invention can be labeled with a detectable label, e.g., a radiolabel by conventional procedures, and provide a quantitative measurement of activated B-cells in biological samples or in vivo.

Because of its specificity for neoplasms of B-cell origin corresponding to the mid-stage of B-cell differentiation, the monoclonal antibody of the invention can be used to detect the presence of these cell types in biological samples. The monoclonal antibody of the invention can be used as a diagnostic aid in characterizing the cell type of various lymphomas and leukemias arising from B-cells. In addition, in vivo imaging using rodiolabeled monoclonal antibody of the invention can provide a noninvasive means for detecting and localizing these cell types, e.g., lymphoid tumors.

The monoclonal antibody of the invention will also be useful in defining the role of activated B-cells in autoimmune diseases, infections and other diseases which are characterized by activated B-cells, e.g., organ rejection.

Other embodiments are within the following claims.

What is claimed is:

1. A monoclonal antibody recognizing an antigenic determinant on activated human B-cells, said antigenic determinant being characterized in that it is a protein distinct from B-LAST-1 and BB-1 and is a protein on the surface of activated B-cells having an apparent molecular weight of approximately 75,000 daltons under reducing conditions and 67,000 daltons under non-reducing conditions, said antibody being a protein of the IgM isotype and being reactive with less than 1% of unstimulated human B-cells, with less than 6% of stimulated or resting T-cells and monocytes, and unreactive with neoplasms of non-B-cell origin, or neoplasms of B-cell origin corresponding to stages of differentiation other than the mid-stage of B-cell differentiation.

2. The antibody of claim 1, said antigenic determinant being obtained from peripheral or splenic human B-cells activated with Epstein-Barr virus, pokeweed mitogen, protein A, or anti-immunoglobulin, or from Burkitt's lymphoma cell line Ramos or the plasma cell leukemia line RPMI 8226.

3. A hybridoma cell capable of producing the monoclonal antibody of claim 1.

4. A monoclonal antibody as claimed in claim 1, said antibody being produced by a hybridoma cell line having the identifying characteristics of ATCC No. HB 8716.

5. Hybridoma cell line capable of producing an antibody as claimed in claim 1, said cell line being identified as ATCC No. 8716.

6. The antibody of claim 1, said antibody being labeled with a detectable label.

7. The antibody of claim 6, said label being radiolabeled.

8. A hybridoma cell having the identifying characteristics of ATCC No. HB 8716.

9. A substantially pure protein having an antigenic determinant or determinants identical to determinants of a single-chain polypeptide having an apparent molecular weight of approximately 75,000 daltons under reducing conditions and 67,000 daltons under non-reducing conditions, said single-chain polypeptide being a protein on the surface of activated human B-cells.

10. A protein as claimed in claim 9 which is obtained from peripheral or splenic human B-cells activated with Epstein-Barr virus, pokeweed mitogen, protein A, or anti-immunoglobulin, or from Burkitt's lymphoma cell line Ramos or the plasma cell leukemia line RPMI 8226.

11. A protein as claimed in any of claims 9, or 10 which is detectably labeled.

12. A protein as claimed in any of claims 9, or 10 which is bound to an insoluble phase.

13. The method of assaying a biological specimen for the presence of antibodies to cells expressing the protein of claim 9, which comprises incubating said specimen with the protein of claim 9 and determining whether or not an immunocomplex is formed.

14. A kit for assaying a sample for the presence of antibody to cells expressing the protein of claim 9, said kit being compartmentalized to receive in close confinement therein one or more containers which comprise a first container containing said protein, and a second container containing a means for detecting the formation of an immunocomplex between said antibody and said protein.

15. The method of assaying a biological specimen for the presence of cells expressing the protein of claim 9, which comprises incubating said specimen with a monoclonal antibody recognizing an antigenic determinant on activated human B-cells, said antigenic determinant being characterized in that it is a protein distinct from B-LAST-1 and BB-1 and is a protein on the surface of activated B-cells having an apparent molecular weight of approximately 75,000 daltons under reducing conditions and 67,000 daltons under non-reducing conditions, said antibody being a protein of the IgM isotype and being reactive with less than 1% of unstimulated human B-cells, with less than 6% of stimulated or resting T-cells and monocytes, and unreactive with neoplasms of non-B-cell origin, or neoplasms of B-cell origin corresponding to stages of differentiation other than the mid-stage of B-cell differentiation, and determining whether or not an immunocomplex is formed.

16. The method as claimed in claim 15 wherein said specimen comprises human peripheral blood, bone marrow or lymphoid tissue.

17. The method as claimed in claim 15 wherein said specimen comprises human B-cells, or neoplasms of B-cell origin.

18. The method of claim 15 wherein said antigenic protein is obtained from peripheral or splenic human B-cells activated with Epstein-Barr virus, pokeweed mitogen, protein A, or anti-immunoglobulin, or from Burkitt's lymphoma cell line Ramos or the plasma cell leukemia line RPMI 8226.

19. The method as claimed in claim 15 wherein said specimen comprises human blood.

20. The method as claimed in claim 15 in which said monoclonal antibody is produced by a hybridoma cell line having the identifying characteristics of ATCC No. HB 8716.

21. A kit for assaying a sample for the presence of cells expressing the protein of claim 9, said kit being compartmentalized to receiving in close confinement therein one or more containers which comprise a first container containing a monoclonal antibody recognizing an antigenic determinant on activated human B-cells, said antigenic determinant being characterized in that it is a protein distinct from B-LAST-1 and BB-1 and is a protein on the surface of activated B-cells having an apparent molecular weight of approximately 75,000 daltons under reducing conditions and 67,000 daltons under non-reducing conditions, said antibody being a protein of the IgM isotype and being reactive with less than 1% of unstimulated human B-cells, with less than 6% of stimulated or resting T-cells and monocytes, and unreactive with neoplasms of non-B-cell origin, or neoplasms of B-cell origin corresponding to stages of differentiation other than the mid-stage of B-cell differentiation, and a second container containing a means for detecting the formation of an immunocomplex between said antibody and said protein.

22. A kit as claimed in claim 21 in which said monoclonal antibody is produced by a hybridoma cell line having the identifying characteristics of ATCC No. HB 8716.

* * * * *

UNITED STATES PATENT AND TRADEMARK OFFICE
CERTIFICATE OF CORRECTION

PATENT NO. : 4,692,405
DATED : September 8, 1987
INVENTOR(S) : Arnold Freedman et al.

It is certified that error appears in the above-identified patent and that said Letters Patent are hereby corrected as shown below: On the Title Page:

Under "OTHER PUBLICATIONS", "Frisman et al., Blood, Vol. 62, 124-1229 (1982)" should be --Frisman et al., Blood, Vol. 62, 1224-1229 (1983)--;

Col. 8, line 25, after "SEPHAROSE", add --4B--;

Col. 8, line 26, delete "beads" before "SEPHAROSE";

Col. 8, lines 30-31, delete "(octyl phenoxy polyethoxy ethanol)" in line 30 and place it after "100" in line 31;

Col. 8, line 38, delete "4B" before "(lanes 1 and 5)".

Signed and Sealed this

Twenty-third Day of February, 1988

*Attest:*

DONALD J. QUIGG

*Attesting Officer*   *Commissioner of Patents and Trademarks*